United States Patent [19]

Patience et al.

[11] Patent Number: 4,983,173
[45] Date of Patent: Jan. 8, 1991

[54] SURGICAL SPONGE

[75] Inventors: Donald Patience, Cary; Felipe S. Li, Lake Zurich, both of Ill.

[73] Assignee: The Kendall Company, Boston, Mass.

[21] Appl. No.: 816,545

[22] Filed: Jan. 6, 1986

Related U.S. Application Data

[63] Continuation of Ser. No. 472,454, Mar. 7, 1983, abandoned.

[51] Int. Cl.$^5$ ............................................. A61F 13/54
[52] U.S. Cl. .................................................... 604/384
[58] Field of Search ............... 604/378, 381, 383, 384; 139/408–410, 413–415

[56] References Cited

U.S. PATENT DOCUMENTS

| | | | |
|---|---|---|---|
| Re. 26,515 | 1/1969 | Holliday et al. | 604/384 |
| 3,104,684 | 9/1963 | Seltzer | 604/384 |
| 3,459,186 | 8/1969 | Schwartz | 604/378 |
| 3,568,676 | 3/1971 | Del Guercio | 604/378 |
| 3,747,601 | 7/1973 | May, Jr. | 604/384 |
| 3,756,241 | 9/1973 | Patience | 604/362 |
| 4,036,234 | 7/1977 | Ishizuka | 604/378 |

*Primary Examiner*—C. Fred Rosenbaum
*Attorney, Agent, or Firm*—Alvin Isaacs

[57] ABSTRACT

A surgical sponge comprising, a sheet of absorbent material comprising a plurality of layers of an open mesh gauze fabric having generally parallel woven spaced warp and filling yarns. The sheet has one or more spaced generally parallel tie-in yarns interwoven between the layers in at least one direction of the sheet, with a substantial number of the yarns in one layer generally parallel to the tie-in yarns being located intermediate the corresponding yarns in another layer of the sheet to define a staggered configuration of the sheet yarns, with the tie-in yarns limiting freedom of movement of the staggered woven yarns to retain them in place, and with the sheet being folded into a multiple ply configuration.

4 Claims, 1 Drawing Sheet

SURGICAL SPONGE

This is a continuation of abandoned application No. 472,454, filed Mar. 7, 1983.

BACKGROUND OF THE INVENTION

The present invention relates to medical devices, and more particularly to surgical sponges and wound dressings.

This invention is concerned with wound dressings and surgical sponges, such as ABD packs, or abdominal packs. Surgical sponges and wound dressings have evolved over many years of surgical practice. Presently used sponges and dressings are an attempt to retain both the advantages of thin, soft and flexible single layers and the absorptive cushioning and insulating properties of thicker padlike structures. As a result, the sponges and dressings have traditionally been formed of multiple layers of thin, soft, low-count gauzelike material which are unified along fairly widely separated lines usually extending longitudinally or transversely but in some instances in both directions. Unification has been accomplished either by lines of machine stitching whether the pack is formed of separated layers or, as is more common, by folding a single width of fabric, or by interweaving yarns in various layers of the multi-ply fabric as set forth in U.S. patent application Ser. No. 250,238, filed May 4, 1972, of common assignee, now abandoned, a continuation-in-part of Ser. No. 093,191 filed Nov. 27, 1970, now abandoned. Another sponge is disclosed in U.S. Pat. No. 3,756,241, incorporated herein by reference.

Although such sponges and dressings have been found useful in the past, it is desirable to improve the fluid transfer characteristics of the sponges and dressings, and minimize snagging of the sponges and dressings. Also, it is desirable to make the sponges and dressings both absorbent and nonadherent to the wound. As used hereinafter, the term "surgical sponges" will include wound dressings.

SUMMARY OF THE INVENTION

A principal feature of the present invention is the provision of an improved surgical sponge of simplified construction.

The sponge of the present invention comprises, a sheet of absorbent material comprising a plurality of layers of an open mesh gauze fabric having generally parallel woven spaced warp and filling yarns. The sheet has one or more spaced generally parallel tie-in yarns interwoven between the layers in at least one direction of the sheet, with a substantial number of the yarns in one layer generally parallel to the tie-in yarns being located intermediate the corresponding yarns in another layer of the sheet to define a staggered configuration of the sheet yarns, and with the sheet being folded into a multiple ply configuration.

A feature of the present invention is that the tie-in yarns limit freedom of movement of the staggered woven yarns to retain them in place.

Another feature of the invention is that the staggered yarns give the sponge an appearance of a high count gauze material.

Yet another feature of the invention is that the staggered yarns improve the fluid transfer characteristics of the sponge and facilitates absorbing body fluids.

Another feature of the invention is that the tie-in yarns minimize the snagging of the sheet.

A further feature of the invention is that the sponge improves wicking into an inner layer due to the tie-in yarns which are part of both layers.

Yet another feature of the invention is that an outer layer of the sponge may be constructed from a hydrophobic material and an inner layer can be constructed from a hydrophilic material, such that the sponge is both absorbent and nonadherent to a wound.

Still another feature of the invention is that different layers may have different sized yarns in order to texturize the sheet and provide different abrasion and conformability characteristics in the layers.

Further features will become more fully apparent in the following description of the embodiments of this invention and from the appended claims.

DESCRIPTION OF THE PREFERRED EMBODIMENTS

Figure 1:
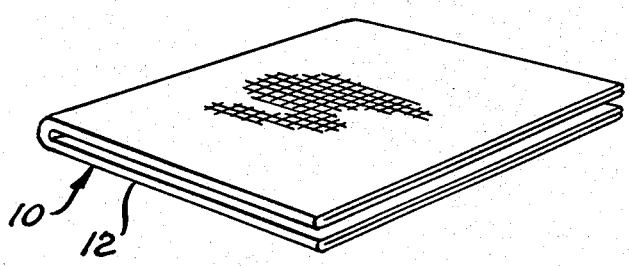
FIG. 1 is a perspective view of a surgical sponge of the present invention.
Figure 2:
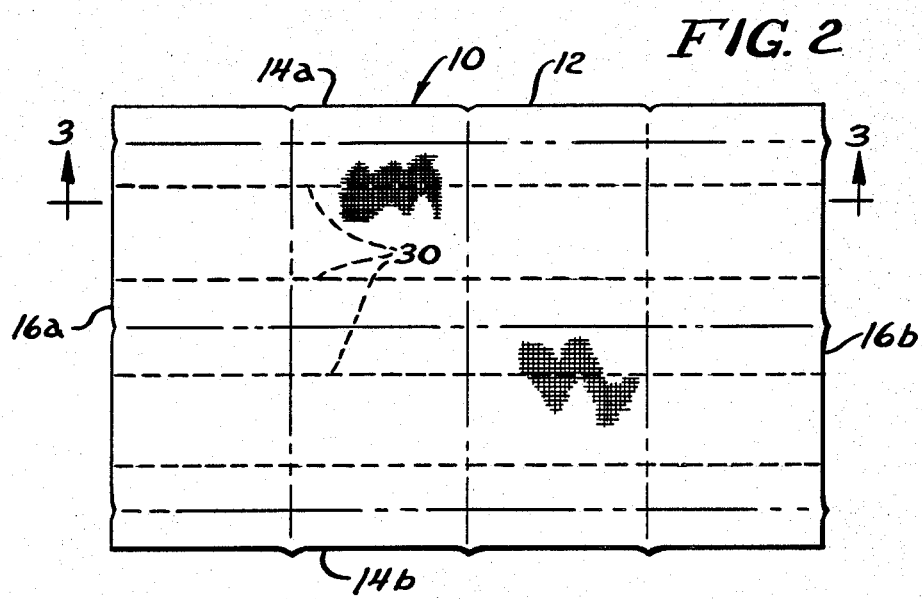
FIG. 2 is a plan view of a sheet in the sponge of FIG. 1.
Figure 3:
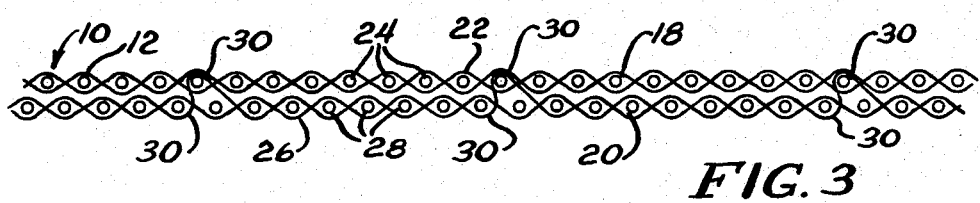
FIG. 3 is a fragmentary sectional view taken substantially as indicated along the line 3—3 of FIG. 2.

Referring now to FIGS. 1-3, there is shown a surgical sponge generally designated 10 comprising a sheet 12 of absorbent material being folded into a multiple ply configuration, as shown in FIG. 1. With reference to FIGS. 1-3, the sheet 12 has a pair of opposed side edges 14a and 14b, and a pair of opposed end edges 16a and 16b connecting the side edges 14a and b. The sheet 12 has a first layer 18 of open mesh gauze fabric having a plurality of generally parallel woven spaced warp yarns 22 extending between the end edges 16a and b, and a plurality of generally parallel woven spaced filling yarns 24 extending between the side edges 14a and b. The sheet 12 has a second layer 20 of an open mesh gauze fabric having a plurality of generally parallel woven spaced warp yarns 26 extending between the end edges 16a and b, and a plurality of generally parallel woven spaced filling yarns 28 extending between the side edges 14a and b.

Figure 4:
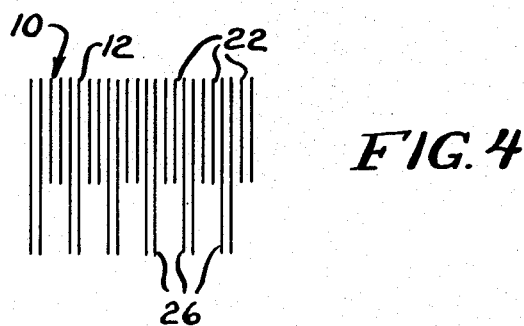
FIG. 4 is a fragmentary plan view taken on an enlarged scale of generally parallel warp yarns of the sheet of FIG. 2.

The sheet 12 has a plurality of spaced generally parallel tie-in yarns 30 which are interwoven between the layers 18 and 20 in the warp direction of the sheet 12. Of course, in an alternative form, the sheet 12 could have tie-in filling yarns which are interwoven between the layers 18 and 20 of the sheet 12. With reference to FIG. 4, a substantial number of the warp yarns 22 in the layer 18 which are generally parallel to the tie-in yarns 30 are located intermediate the corresponding warp yarns 26 of the layer 20 of the sheet 12 to define a staggered configuration of the warp yarns 22 and 26. The tie-in yarns 30 limit freedom of movement of the staggered woven yarns 22 and 26 in order to retain them in place. Of course, the filling yarns 24 and 28 also may be staggered in the sheet 12. In any event, the staggered yarns give the sheet 12 an appearance of high count gauze, and improve the fluid transfer characteristics in the sponge 10, while the tie-in yarns 30 minimize snagging of the sheet 12.

With reference to FIGS. 1-3, in an alternative embodiment of the invention, the layer 18 may be woven from hydrophobic yarns, such as polyester, and the layer 20 may be woven from hydrophilic yarns, such as cotton. When the sheet 12 is folded into the multiple ply configuration, the hydrophobic layer 18 faces outwardly from the folded sheet in order to define a nonadherent surface of the sponge 10 for contacting a wound on a patient, while the inner hydrophilic layer 20 provides absorbency for the sponge.

With reference to FIGS. 1-3, in yet another embodiment of the invention, the first layer 18 may be woven from yarns of a different size from the yarns in the second layer 20. In this embodiment, the different sized yarns texturize the fabric, and provide different abrasion characteristics in the layers 18 and 20.

The foregoing detailed description is given for clearness of understanding only, and no unnecessary limitations should be understood therefrom, as modifications will be obvious to those skilled in the art.

We claim:

1. A surgical sponge, comprising:
    a sheet of absorbent material comprising only two layers of an open mesh gauze fabric having generally parallel woven spaced warp and filling yarns, with a first layer in the sheet comprising totally hydrophobic yarns and defining a first outer surface of the sheet, with a second layer of the sheet comprising substantially hydrophilic yarns and defining a second opposed outer surface of the sheet, with said sheet being folded into a multiple ply configuration, and with the first layer of hydrophobic yarns solely facing outwardly from the folded sheet, wherein the sheet has one or more spaced generally parallel tie-in yarns interwoven between the layers in at least one direction of the sheet.

2. The sponge of claim 1 wherein the hydrophobic layer comprises polyester yarns.

3. The sponge of claim 1 wherein the hydrophilic layer comprises cotton yarns.

4. The sponge of claim 1 wherein the sheet has two layers.

* * * * *